US010575721B2

(12) United States Patent
Yamazaki (10) Patent No.: US 10,575,721 B2
(45) Date of Patent: Mar. 3, 2020

(54) IMAGE PICKUP SYSTEM AND IMAGE PROCESSING APPARATUS

(71) Applicant: OLYMPUS CORPORATION, Tokyo (JP)

(72) Inventor: Ryuichi Yamazaki, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 118 days.

(21) Appl. No.: 16/014,030

(22) Filed: Jun. 21, 2018

(65) Prior Publication Data

US 2018/0296078 A1 Oct. 18, 2018

Related U.S. Application Data

(63) Continuation of application No. PCT/JP2016/086514, filed on Dec. 8, 2016.

(30) Foreign Application Priority Data

Dec. 24, 2015 (JP) .................................. 2015-252028

(51) Int. Cl.
*A61B 1/06* (2006.01)
*H04N 5/232* (2006.01)
(Continued)

(52) U.S. Cl.
CPC ........ *A61B 1/0638* (2013.01); *A61B 1/00009* (2013.01); *A61B 1/0646* (2013.01);
(Continued)

(58) Field of Classification Search
CPC . A61B 1/0638; A61B 1/0646; A61B 1/00009; G02B 23/2461; H04N 9/07; H04N 5/232; H04N 5/2256; H04N 2005/2255
See application file for complete search history.

(56) References Cited

U.S. PATENT DOCUMENTS 7,179,222 B2 * 2/2007 Imaizumi ........... A61B 1/00009
600/109
8,000,776 B2 * 8/2011 Gono ................. A61B 1/00009
600/109
(Continued)

FOREIGN PATENT DOCUMENTS

CN 106714657 A 5/2017
EP 3 175 774 A1 6/2017
(Continued)

OTHER PUBLICATIONS

Extended Supplementary European Search Report dated Jun. 26, 2019 in European Patent Application No. 16 87 8384.3.
(Continued)

*Primary Examiner* — James M Pontius
(74) *Attorney, Agent, or Firm* — Scully, Scott, Murphy & Presser, P.C.

(57) ABSTRACT

An image pickup system includes a light source unit configured to perform illumination; an image pickup unit configured to output an image pickup signal; a pre-processing unit configured to generate a first image signal, a second image signal, and a third image signal, each corresponding to one field, and sequentially output the image signals; and a synchronization processing unit configured to selectively assign the image signals sequentially outputted to a first color channel, a second color channel, and a third color channel. The synchronization processing unit switches first assignment processing for assigning the first image signal to the first color channel and further assigning the second image signal to the second and third color channels and second assignment processing for assigning the first image signal to the first color channel and further assigning the third image signal to the second and third color channels.

10 Claims, 4 Drawing Sheets

(51) Int. Cl.
  *H04N 9/07* (2006.01)
  *G02B 23/24* (2006.01)
  *A61B 1/00* (2006.01)
  *H04N 5/225* (2006.01)

(52) U.S. Cl.
  CPC ....... *G02B 23/2461* (2013.01); *H04N 5/2256* (2013.01); *H04N 5/232* (2013.01); *H04N 9/07* (2013.01); *H04N 2005/2255* (2013.01)

(56) References Cited

U.S. PATENT DOCUMENTS

| | | | |
|---|---|---|---|
| 9,107,603 B2* | 8/2015 | Kaku | A61B 1/00009 |
| 10,321,103 B2* | 6/2019 | Mizuno | A61B 1/04 |
| 10,419,693 B2* | 9/2019 | Yamamoto | G02B 21/365 |
| 2010/0217077 A1* | 8/2010 | Gono | A61B 1/00096 |
| | | | 600/109 |
| 2010/0259552 A1* | 10/2010 | Hsu | G09G 3/3413 |
| | | | 345/592 |
| 2013/0286175 A1 | 10/2013 | Hashimoto et al. | |
| 2013/0338438 A1 | 12/2013 | Watanabe | |
| 2014/0105493 A1* | 4/2014 | Wu | G06T 9/00 |
| | | | 382/166 |
| 2016/0360125 A1* | 12/2016 | Yamamoto | A61B 1/06 |
| 2017/0180682 A1 | 6/2017 | Mizuno et al. | |
| 2018/0000335 A1* | 1/2018 | Igarashi | A61B 1/04 |

FOREIGN PATENT DOCUMENTS

| | | |
|---|---|---|
| JP | 5326065 B2 | 10/2013 |
| JP | 2013-248319 A | 12/2013 |
| JP | 2014-050595 A1 | 3/2014 |

OTHER PUBLICATIONS

International Search Report dated Mar. 7, 2017 issued in PCT/JP2016/086514.

* cited by examiner

| IMAGE DATA STORED IN MEMORY | GD0 | BD0 | BD0' |
|---|---|---|---|
| COMBINATION OF DATA USED AFTER SYNCHRONIZATION IN CONVENTIONAL EXAMPLE | GD0 | BD0 | BD0' 0.0 – 1.0 |
| COMBINATION OF DATA USED AFTER SYNCHRONIZATION IN PRESENT EMBODIMENT | GD0 | BD0 | BD0' 0.0 – 1.0 |

FIG. 4B

| IMAGE DATA STORED IN MEMORY | BD0 | BD0' | GD1 |
|---|---|---|---|
| COMBINATION OF DATA USED AFTER SYNCHRONIZATION IN CONVENTIONAL EXAMPLE | BD0 | BD0' 0.0 – 1.0 | GD1 |
| COMBINATION OF DATA USED AFTER SYNCHRONIZATION IN PRESENT EMBODIMENT | BD0 0.0 – 1.0 | BD0' | GD1 |

FIG. 4C

| IMAGE DATA STORED IN MEMORY | BD0' | GD1 | BD1 |
|---|---|---|---|
| COMBINATION OF DATA USED AFTER SYNCHRONIZATION IN CONVENTIONAL EXAMPLE | BD0' 0.0 – 1.0 | GD1 | BD1 |
| COMBINATION OF DATA USED AFTER SYNCHRONIZATION IN PRESENT EMBODIMENT | BD0' 0.0 – 1.0 | GD1 | BD1 |

IMAGE PICKUP SYSTEM AND IMAGE PROCESSING APPARATUS

CROSS REFERENCE TO RELATED APPLICATION

This application is a continuation application of PCT/JP2016/086514 filed on Dec. 8, 2016 and claims benefit of Japanese Application No. 2015-252028 filed in Japan on Dec. 24, 2015, the entire contents of which are incorporated herein by this reference.

BACKGROUND OF INVENTION

1. Field of the Invention

The present invention relates to an image pickup system and an image processing apparatus, and particularly to an image pickup system and an image processing apparatus which sequentially irradiate illumination lights in a plurality of wavelength bands different from one another to pick up an image of an object.

2. Description of the Related Art

In a medical field, an operation using a device, which is minimally invasive for a living body, such as an endoscope has been conventionally performed.

As an observation method using an endoscope, there have been conventionally known methods for observation such as normal light observation for irradiating an object within a living body with light in each of colors, i.e., R (red), G (green), and B (blue) to obtain an image having a substantially similar color tone to that in observation with naked eyes, and narrow band light observation for irradiating an object within a living body with light in a narrower band than illumination light for normal light observation to obtain an image in which a blood vessel or the like existing in a superficial portion of the mucous membrane of the living body is highlighted.

Japanese Patent No. 5326065, for example, discloses an endoscope device which performs narrow band light observation using a rotation filter having a filter using a G (green) wavelength band as a transmission band and two filters each using a B (blue) wavelength band as a transmission band with the filters being provided at an equal angle in its peripheral direction, and a narrow band filter configured to emit light emitted from a light source to the rotation filter using a band of the light as a narrow band.

The endoscope device disclosed in Japanese Patent No. 5326065 is configured as a device which performs a frame-sequential operation to sequentially irradiate illumination light in a G wavelength band and illumination light in a B wavelength band to pick up an image of an object and generates a display image corresponding to one frame using images corresponding to a plurality of fields obtained by picking up the object image.

More specifically, Japanese Patent No. 5326065 discloses a configuration for performing image pickup with G illumination light and image pickup with B1 and B2 illumination lights, acquiring a G pickup image based on return light of the G illumination light and B1 and B2 pickup images based on return lights of the B1 and B2 illumination lights, subjecting the pickup images to predetermined calculation to find a synthesis signal, and displaying a pickup image for narrow band light observation on a monitor.

SUMMARY OF THE INVENTION

An image pickup system according to an aspect of the present invention is an image pickup system which sequentially irradiates illumination lights of a plurality of colors to pick up an image of an object, and includes a light source unit configured to perform illumination with first illumination light in a wavelength band of a first color and perform illumination with second illumination light in a wavelength band of a second color which is different from the wavelength band of the first color and third illumination light in the wavelength band of the second color emitted temporally after the second illumination light, within a predetermined time period, an image pickup unit configured to pick up an image of return light from an object image illuminated with the illumination light emitted from the light source unit for each predetermined period and output an image pickup signal, an image generation unit configured to generate a first image signal responsive to return light of the first illumination light, a second image signal responsive to return light of the second illumination light, and a third image signal responsive to return light of the third illumination light, each corresponding to one field, and sequentially output the image signals, and an assignment unit configured to selectively assign the image signals sequentially outputted from the image generation unit to a first color channel, a second color channel, and a third color channel, in which the assignment unit switches first assignment processing for assigning the first image signal to the first color channel and further assigning the second image signal to the second and third color channels and second assignment processing for assigning the first image signal to the first color channel and further assigning the third image signal to the second and third color channels in each of field periods constituting one frame.

An image processing apparatus according to an aspect of the present invention includes an image generation unit configured to generate, based on an image pickup signal outputted from an image pickup unit configured to pick up an image of return light from an object image illuminated with illumination light emitted from a light source unit configured to perform illumination with first illumination light in a wavelength band of a first color and perform illumination with second illumination light in a wavelength band of a second color which is different from the wavelength band of the first color and third illumination light in the wavelength band of the second color emitted temporally after the second illumination light within a predetermined time period for each predetermined period and output the image pickup signal, a first image signal responsive to return light of the first illumination light, a second image signal responsive to return light of the second illumination light, and a third image signal responsive to return light of the third illumination light, each corresponding to one field, and sequentially output the image signals; and an assignment unit configured to selectively assign the image signals sequentially outputted from the image generation unit to a first color channel, a second color channel, and a third color channel, in which the assignment unit switches first assignment processing for assigning the first image signal to the first color channel and further assigning the second image signal to the second and third color channels and second assignment processing for assigning the first image signal to the first color channel and further assigning the third image signal to the second and third color channels in each of field periods constituting one frame.

DETAILED DESCRIPTION OF THE PREFERRED EMBODIMENT(S)

An embodiment of the present invention will be described below with reference to the drawings.

Figure 1:
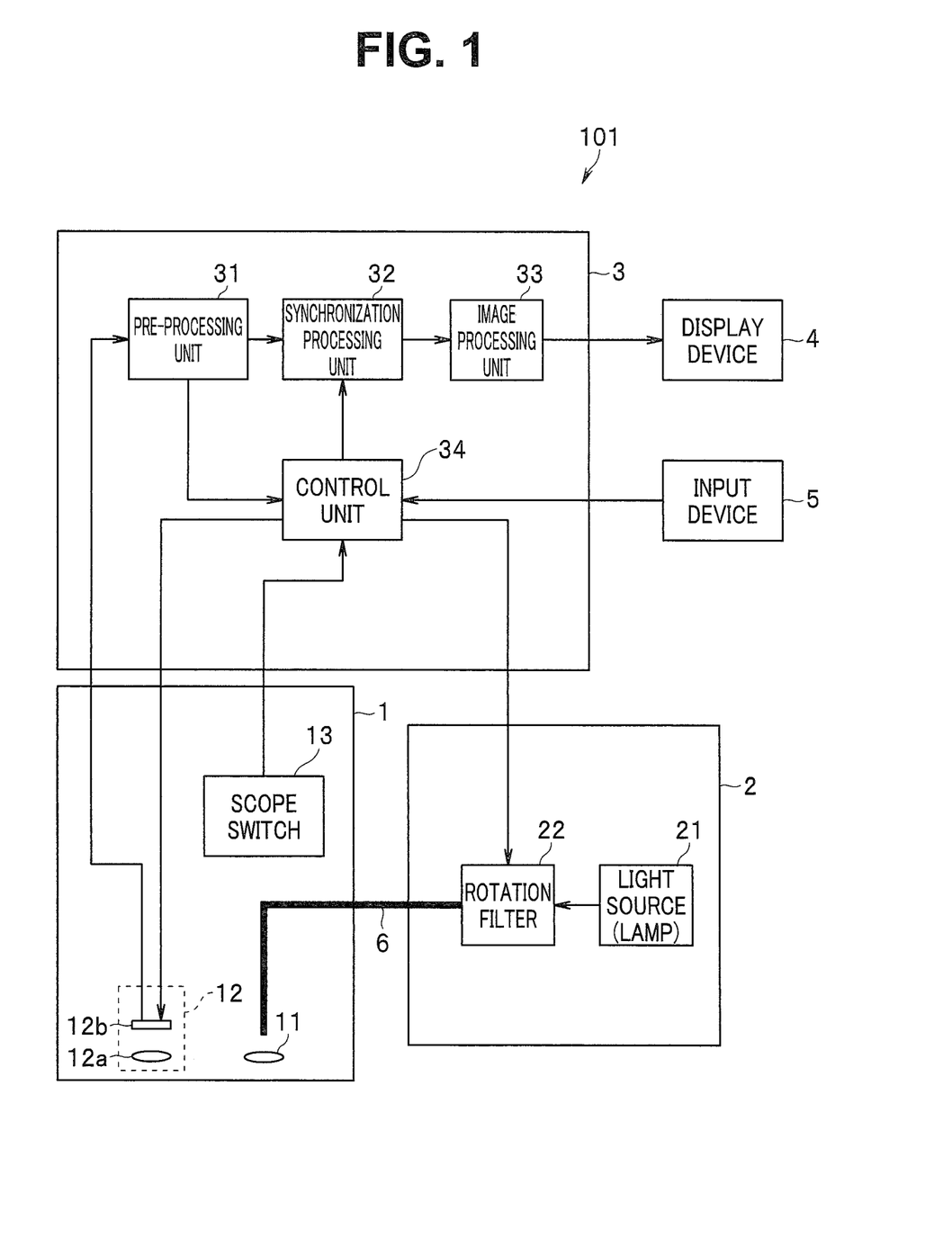
FIG. 1 is a diagram illustrating a configuration of an image pickup system according to an embodiment of the present invention.

FIG. 1 is a diagram illustrating an image pickup system according to an embodiment of the present invention.

An image pickup system 101 is configured to include an endoscope 1 including an insertion section having an elongated shape which can be inserted into a subject, which is a living body, and configured to pick up an image of an object such as a living tissue within the subject and output an image pickup signal; a light source device 2 configured to supply illumination light used to observe the object via a light guide 6 inserted into and arranged in the endoscope 1; a processor 3 serving as an image processing device configured to generate a video signal responsive to the image pickup signal outputted from the endoscope 1; a display device 4 configured to display an image or the like responsive to the video signal outputted from the processor 3; and an input device 5 including a switch and/or a button or the like capable of issuing an instruction or the like responsive to an input operation of a user such as an operator to the processor 3, as illustrated in FIG. 1.

The endoscope 1 is configured by providing, at a distal end portion of the insertion section, an illumination optical system 11 configured to irradiate light transmitted by the light guide 6 to the object and an image pickup unit 12 configured to output an image pickup signal obtained by picking up an image of return light emitted from the object in response to the light irradiated from the illumination optical system 11. Also, the endoscope 1 is configured to include a scope switch 13 capable of issuing various instructions respectively responsive to user's operations to the processor 3.

The image pickup unit 12 is configured to pick up an image of the return light from the object illuminated with the illumination light emitted from the light source device 2 for each predetermined period and output an image pickup signal. More specifically, the image pickup unit 12 is configured to include an objective optical system 12a configured to form an image of the return light emitted from the object and an image pickup device 12b arranged such that its image pickup surface for receiving the return light matches an image formation position of the objective optical system 12a.

The image pickup device 12b is composed of a CCD or a CMOS, for example, and is configured to be driven in responses to an image pickup device driving signal outputted from the processor 3 while sequentially outputting an image pickup signal obtained by picking up an image of the return light from the object which has been formed on the image pickup surface.

A scope switch 13 is provided with an observation mode setting switch (not illustrated) capable of issuing an instruction to set an observation mode of the image pickup system 101 to either one of a white light (normal light) observation mode and a narrow band light observation mode to the processor 3 in response to a user's operation, for example.

The light source device 2 is configured to include a light source 21 composed of a xenon lamp or the like configured to emit white light and a rotation filter 22. The rotation filter 22 is configured to include a rotation filter for white light observation and a rotation filter for narrow band light observation. The rotation filter 22 is configured such that the rotation filter for white light observation or the rotation filter for narrow band light observation is inserted into an optical path of illumination light from the light source 21 based on a switching signal from a control unit 34.

Note that the configuration of the rotation filter 22 is not limited to the configuration including the rotation filters for white light observation and narrow band light observation, but may be another configuration. The light source 21 is not limited to a xenon lamp or the like, but may be an LED (light emitting diode) or a laser diode, for example. Also, the light source 21 may be configured to cause the LED, the laser diode, or the like to irradiate R (red) light, G (green) light, and B (blue) light in a time divisional manner by PWM (pulse width modulation) control, for example, without including the rotation filter.

The rotation filter 22 has a disc shape and has three openings provided at an equal angle in its circumferential direction. Filters are respectively mounted on the three openings. For example, the rotation filter for white light observation is provided with R (red), G (green), and B (blue) filters, and is configured such that R light, G light, and B light are sequentially emitted. Also, the rotation filter for narrow band light observation is provided with G (green), B (blue), and B' (blue) filters, and is configured such that G light, B light, and B' light are sequentially emitted. Note that the B light and the B' light are respectively illumination lights in the same wavelength band.

That is, the light source 21 and the rotation filter 22 constituting a light source unit performs illumination with first illumination light (G light) in a first band while performing illumination with second illumination light (B light) in a second band and third illumination light (B) in the second band emitted temporally after the second illumination light. Note that although a frame-sequential image pickup system is described in the present embodiment, the present invention is not limited to this, but may be applied to a simultaneous image pickup system.

The rotation filter 22 has its center mounted on a rotational axis of a rotating motor (not illustrated), and is configured to be driven to rotate. The rotation filter 22 is configured to rotate at a predetermined speed based on a control signal from the control unit 34.

The illumination light emitted from the rotation filter 22 is incident on an incidence end of the light guide 6, and is irradiated toward the object from the distal end portion of the insertion section in the endoscope 1. The return light from the object is picked up by the image pickup device 12b, and is supplied as an image pickup signal to the processor 3.

The processor 3 is configured to include a pre-processing unit 31, a synchronization processing unit 32, an image processing unit 33, and a control unit 34.

The pre-processing unit 31 constituting an image generation unit includes a signal processing circuit such as a noise reduction circuit and an A/D (analog-to-digital) conversion circuit, and subjects image pickup signals sequentially outputted from the endoscope 1 to processing such as noise reduction and A/D conversion to generate image data corresponding to one field. The pre-processing unit 31 is configured to sequentially output the generated image data corresponding to one field to the synchronization processing unit 32 and the control unit 34.

The synchronization processing unit 32 is configured as a synchronization circuit including a selector configured to operate in response to a synchronization processing control signal, described below, and a plurality of memories connected to a stage succeeding the selector, for example. Also, the synchronization processing unit 32 stores the image data, corresponding to a plurality of fields, sequentially outputted from the pre-processing unit 31 based on the synchronization processing control signal outputted from the control unit 34.

The synchronization processing unit 32 constituting an assignment unit is configured to selectively assign the stored image data corresponding to the plurality of fields to an R channel corresponding to a red color of the display device 4, a G channel corresponding to a green color of the display device 4, and a B channel corresponding to a blue color of the display device 4 and simultaneously output the assigned image data to the image processing unit 33.

The image processing unit 33 is configured to include an image processing circuit such as a synthesis circuit. Also, the image processing unit 33 synthesizes the image data respectively outputted while being assigned to the R channel, the G channel, and the B channel to generate image data corresponding to one frame. The image processing unit 33 is configured to subject the generated image data corresponding to one frame to predetermined image processing such as gamma correction to generate a video signal and sequentially output the generated video signal to the display device 4.

The control unit 34 is configured to include a CPU (central processing unit) or a control circuit, for example. Also, the control unit 34 is configured to detect an observation mode set in an observation mode setting switch in the scope switch 13, generate an illumination control signal for emitting illumination light responsive to the detected observation mode, and output the generated illumination control signal to the rotation filter 22. Also, the control unit 34 is configured to generate, when it detects that the observation mode has been set to the narrow band light observation mode, synchronization processing control signals for respectively setting frequencies of assignment and updating of the image data on the R channel, the G channel, and the B channel based on a luminance value of image data BD (described below) outputted from the pre-processing unit 31, i.e., an evaluation value acquired from the image data BD and output the generated synchronization processing control signals to the synchronization processing unit 32.

Then, operations of the image pickup system thus configured will be described.

First, a user connects each of the units in the image pickup system 101 to a power supply to power on the unit, and then operates the observation mode setting switch in the scope switch 13, to set the observation mode of the image pickup system 101 to the white light observation mode.

The control unit 34 generates, when it detects that the observation mode is set to the white light observation mode, a control signal for rotating the rotation filter for white light observation at a predetermined speed and outputs the generated control signal to the rotation filter 22. Also, the control unit 34 generates an image pickup device driving signal for picking up an image of the return light from the object for each predetermined period and outputs the generated image pickup device driving signal to the image pickup device 12b. Also, the control unit 34 generates, when it detects that the observation mode is set to the white light observation mode, synchronization processing control signals for respectively setting frequencies of assignment and updating of the image data on the R channel, the G channel, and the B channel and outputs the generated synchronization processing control signals to the synchronization processing unit 32.

The rotation filter for white light observation is provided with an R filter, a G filter, and a B filter. When the rotation filter for white light observation rotates at a predetermined speed, illumination lights, i.e., R light, G light, B light, R light, . . . emitted from the light source device 2 while being irradiated onto the object via the illumination optical system 11 are switched in this order and for each predetermined period.

The image pickup device 12b picks up an image of the return light from the object illuminated with the illumination light emitted from the light source device 2 for each predetermined period and outputs an image pickup signal based on the image pickup device driving signal outputted from the control unit 34. That is, according to such an operation of the image pickup device 12b, return light received in a period during which the R light is illuminated, return light received in a period during which the G light is irradiated, and return light received in a period during which the B light is irradiated are each picked up once.

The pre-processing unit 31 generates, based on the image pickup signal outputted from the image pickup device 12b, image data RD responsive to the return light of the R light, image data GD responsive to the return light of the G light, and image data BD responsive to the return light of the B light, each corresponding to one field, and sequentially outputs the generated image data to the synchronization processing unit 32 and the control unit 34.

The synchronization processing unit 32 stores the image data RD, GD, and BD, each corresponding to one field, sequentially outputted from the pre-processing unit 31 based on the synchronization processing control signal outputted from the control unit 34. The synchronization processing unit 32 assigns the stored image data RD corresponding to one field to the R channel, assigns the stored image data GD corresponding to one field to the G channel, and assigns the stored image data BD corresponding to one field to the B channel, and simultaneously outputs the image data to the image processing unit 33. Also, the synchronization processing unit 32 sequentially performs an operation for updating the image data RD assigned to the R channel once, an operation for updating the image data GD assigned to the G channel once, and an operation for updating the image data BD assigned to the B channel once based on the synchronization processing control signal outputted from the control unit 34.

The image processing unit 33 synthesizes the image data RD assigned to the R channel, the image data GD assigned to the G channel, and the image data BD assigned to the B channel, to generate RGB color image data corresponding to one frame. The image processing unit 33 subjects the generated RGB color image data corresponding to one frame to predetermined image processing such as gamma correction to respectively generate video signals, and sequentially outputs the generated video signals to the display device 4.

On the other hand, the user inserts the insertion section in the endoscope 1 into the subject while looking at the image displayed on the display device 4 with the observation mode of the image pickup system 101 set to the white light observation mode, to arrange the distal end portion of the insertion section in the vicinity of a desired object. Then, the user operates the observation mode setting switch in the scope switch 13 with the distal end portion of the insertion section in the endoscope 1 arranged in the vicinity of the desired object, to set the observation mode of the image pickup system 101 to the narrow band light observation mode.

Figure 2:
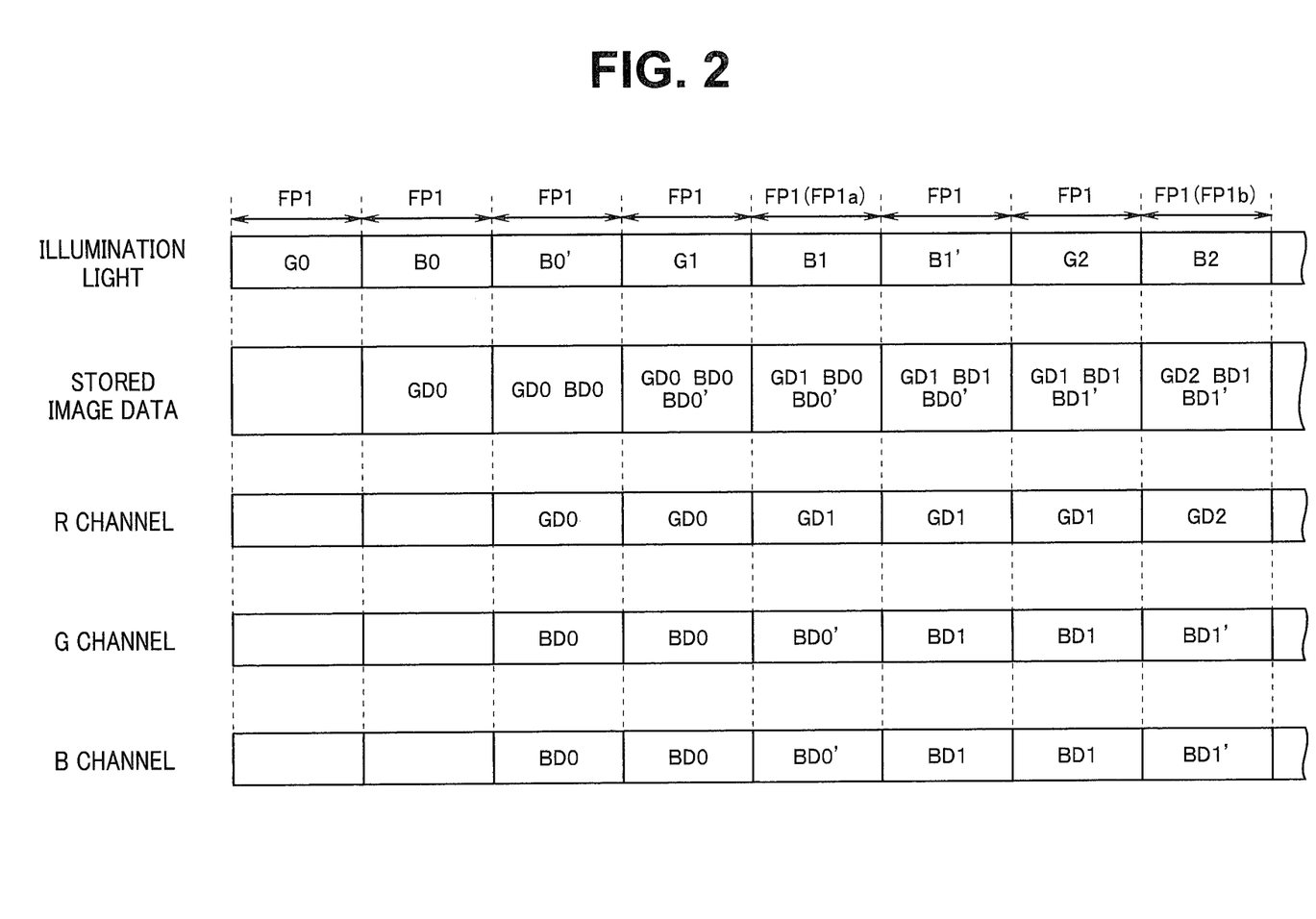
FIG. 2 is a diagram for describing an example of an operation at the time of a narrow band light observation mode.

FIG. 2 is a diagram for describing one example of operations at the time of the narrow band light observation mode. The control unit 34 generates, when it detects that the observation mode is set to the narrow band light observation mode, a control signal for rotating the rotation filter for narrow band light observation at a predetermined speed and outputs the generated control signal to the rotation filter 22. Also, the control unit 34 generates an image pickup device driving signal for picking up an image of return light from the object for each predetermined period FP1 and outputs the generated image pickup device driving signal to the image pickup device 12b. Also, the control unit 34 generates, when it detects that the observation mode is set to the narrow band light observation mode, synchronization processing control signals for respectively setting assignment and updating of image data on the R channel, the G channel, and the B channel, and outputs the generated synchronization processing control signals to the synchronization processing unit 32.

The rotation filter for narrow band light observation is provided with the G filter, the B filter, and the B' filter. When the rotation filter for narrow band light observation rotates at a predetermined speed, illumination lights, i.e., G0 light, B0 light, B0' light, G1 light, . . . emitted from the light source device 2 while being irradiated to the object via the illumination optical system 11 are switched in this order and for each predetermined period FP1, as illustrated in FIG. 2.

The image pickup device 12b picks up an image of the return light from the object illuminated with the illumination light emitted from the light source device 2 for each predetermined period FP1 and outputs an image pickup signal based on the image pickup device driving signal outputted from the control unit 34. That is, according to such an operation of the image pickup device 12b, return light received in a period during which G light is irradiated, return light received in a period during which B light is irradiated, and return light received in a period during which B' light is irradiated are each picked up once.

The pre-processing unit 31 generates, based on the image pickup signal outputted from the image pickup device 12b, image data (a first image signal) GD responsive to the return light of the G light, image data (a second image signal) BD responsive to the return light of the B light, and image data (a third image signal) BD' responsive to the return light of the B' light, each corresponding to one field, and sequentially outputs the generated image data to the synchronization processing unit 32 and the control unit 34.

The synchronization processing unit 32 stores the image data GD, BD, and BD', each corresponding to one field, sequentially outputted from the pre-processing unit 31 based on the synchronization processing control signal outputted from the control unit 34. The synchronization processing unit 32 performs processing for switching an equation (1) and an equation (2), described below, at a predetermined timing and respectively assigning the stored image data corresponding to a plurality of fields to each of the channels in the colors.

Equation 1

$$\begin{pmatrix} R_t \\ G_t \\ B_t \end{pmatrix} = \begin{pmatrix} 1 & 0 & 0 \\ 0 & 1+W & 0 \\ W & 0 & 1 \end{pmatrix} \begin{pmatrix} R_{in} \\ G_{in} \\ B_{in} \end{pmatrix} = \begin{pmatrix} 1 & 0 & 0 \\ 0 & 1+W & 0 \\ W & 0 & 1 \end{pmatrix} \begin{pmatrix} B_2 \\ G \\ B_1 \end{pmatrix} = \begin{pmatrix} B_2 \\ (1+W)G \\ WB_2 + B_1 \end{pmatrix} \quad (1)$$

Equation 2

$$\begin{pmatrix} R_t \\ G_t \\ B_t \end{pmatrix} = \begin{pmatrix} 1 & 0 & 0 \\ 0 & 1+W & 0 \\ W & 0 & 1 \end{pmatrix} \begin{pmatrix} R_{in} \\ G_{in} \\ B_{in} \end{pmatrix} = \begin{pmatrix} 1 & 0 & 0 \\ 0 & 1+W & 0 \\ 1 & 0 & W \end{pmatrix} \begin{pmatrix} B_2 \\ G \\ B_1 \end{pmatrix} = \begin{pmatrix} B_2 \\ (1+W)G \\ B_2 + WB_1 \end{pmatrix} \quad (2)$$

More specifically, the synchronization processing unit 32 performs assignment processing (second assignment processing) using the equation (2) in a first field period serving as a timing at which the image data GD has been assigned to the R channel (first channel) (a timing at which the image data GD is updated: respective timings of predetermined periods FP1a and FP1b illustrated in FIG. 2), to assign the image data BD' to the G channel (second channel) and the B channel (third channel).

On the other hand, the synchronization processing unit 32 performs assignment processing (first assignment processing) using the equation (1) in a field period other than the first field period serving as the timing at which the image data GD has been assigned to the R channel, to assign the image data BD to the G channel and the B channel.

That is, the synchronization processing unit 32 assigns the stored image data GD corresponding to one field to the R channel and assigns the stored image data BD' corresponding to one field to the G channel and the B channel in the first field period. On the other hand, the synchronization processing unit 32 assigns the stored image data GD corresponding to one field to the R channel and assigns the stored image data BD corresponding to one field to the G channel and the B channel in the field period other than the first field period. The synchronization processing unit 32 thus respectively assigns the image data to the channels in the colors, and simultaneously outputs the image data to the image processing unit 33.

Note that in the above-described equations (1) and (2), W is a variable which is changed depending on a luminance value of the image data BD+the image data BD', and satisfies $0 \leq W \leq 1$. If W=0, single exposure for synchronizing (synthesizing) the image data GD corresponding to one field and the image data BD or BD' corresponding to one field is performed. On the other hand, if $0<W \leq 1$, in addition to synchronizing the image data used in the single exposure, double exposure for synchronizing the image data BD or BD' not used in the single exposure in a predetermined proportion is performed.

More specifically, if a luminance value of the image data BD is less than a predetermined threshold value, W ($0<W \leq 1$) is determined such that BD+BD' *W becomes the predetermined threshold value.

If the luminance value of the image data BD is the predetermined threshold value or more, W=0 in which case single exposure is performed.

In the description, BD and BD' are reversed depending on a frame according to the example. Single exposure and double exposure may be switched by the user.

The image processing unit 33 synthesizes the image data GD assigned to the R channel and the image data BD' assigned to the G channel and the B channel to generate narrow band light image data corresponding to one frame in the first field period. On the other hand, the image processing unit 33 synthesizes the image data GD assigned to the R channel and the image data BD assigned to the G channel and the B channel to generate narrow band light image data corresponding to one frame in the field period other than the first field period. The image processing unit 33 subjects the generated narrow band light image data corresponding to one frame to predetermined image processing such as gamma correction to generate video signals, and sequentially outputs the generated video signals to the display device 4.

Figure 3A:
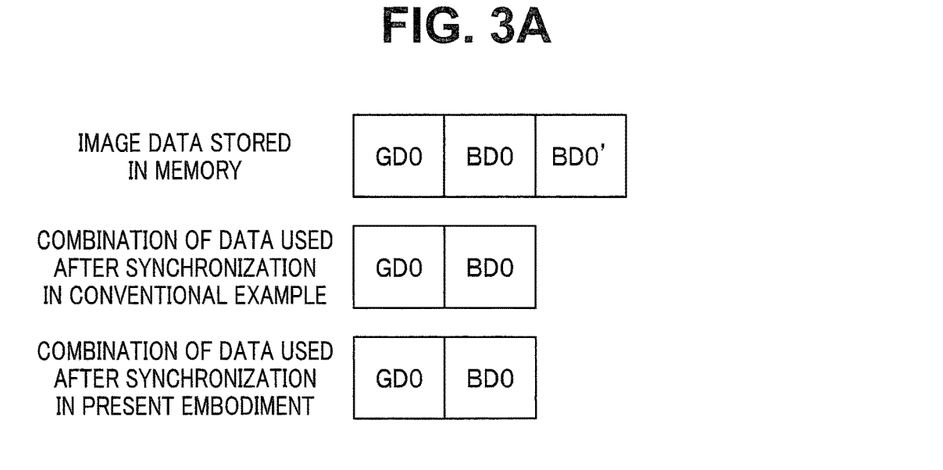
FIG. 3A is a diagram for describing an example of image data synchronized at the time of the narrow band light observation mode.
Figure 3B:
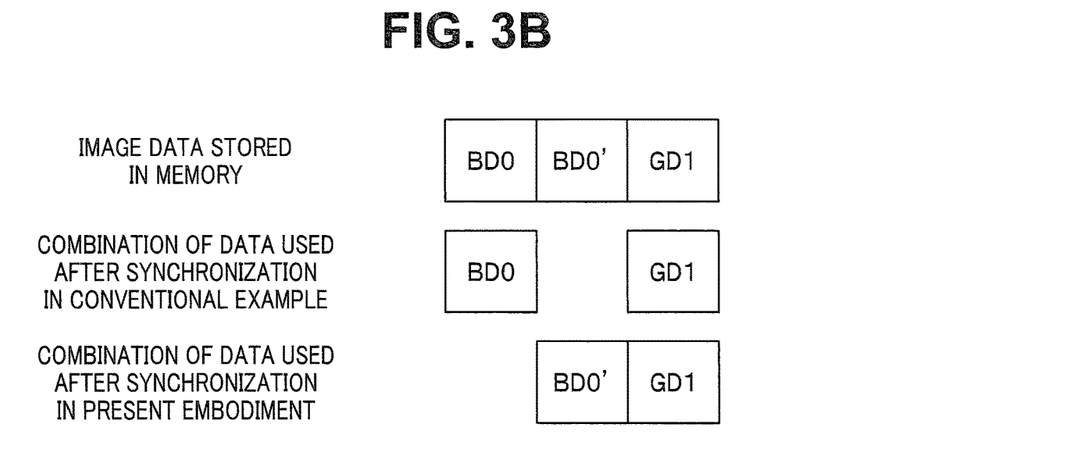
FIG. 3B is a diagram for describing an example of image data synchronized at the time of the narrow band light observation mode.
Figure 3C:
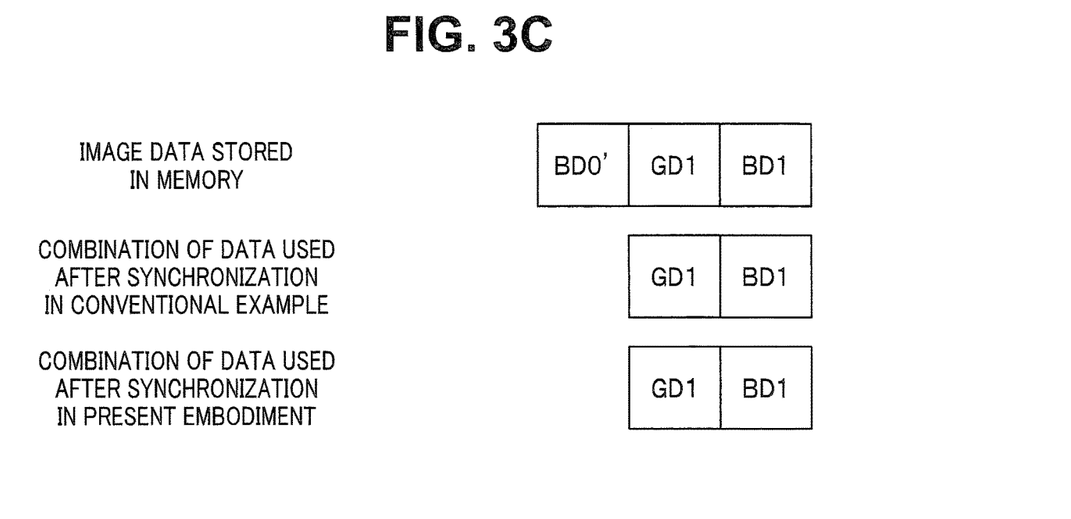
FIG. 3C is a diagram for describing an example of image data synchronized at the time of the narrow band light observation mode.

FIG. 3 is a diagram for describing an example of image data to be synchronized at the time of the narrow band light observation mode. Note that FIG. 3 illustrates an example of image data to be synchronized in the case of the single exposure in which W in the equation (1) and the equation (2) satisfies W=0.

FIG. 3A illustrates a state where image data GD0, BD0, and BD0' sequentially picked up are stored in a memory. In this case, in a conventional example and the present embodiment, assignment processing is performed using the equation (1) so that the image data GD0 and the image data BD0 are synchronized.

FIG. 3B illustrates a state where image data GD1 is further stored in the memory. That is, FIG. 3B illustrates an update timing of the image data GD1. Conventionally, assignment processing has also been performed using the equation (1) at an update timing of the image data GD1. Accordingly, the image data GD and image data BD0 preceding the image data GD1 by two fields have been synchronized, as illustrated in FIG. 3B.

On the other hand, in the present embodiment, an equation to be used for assignment processing is switched from the equation (1) to the equation (2) at the update timing of the image data GD1, and the assignment processing is performed using the equation (2). Accordingly, in the present embodiment, the image data GD1 and image data BD0' preceding the image data GD1 by one field are synchronized, as illustrated in FIG. 3B.

FIG. 3C illustrates a state where the image data BD1 is further stored in the memory. In this case, in the conventional example and the present embodiment, assignment processing is performed using the equation (1) so that the image data GD1 and the image data BD1 are synchronized.

Conventionally, when the state is changed from FIG. 3B to 3C, image data to be synchronized is changed from image data BD0 to image data BD1. Accordingly, the B image data to be synchronized is moved at a stroke, and a backlash is seen occurring at the time of movie observation.

Thus, the updated image data GD1 and the image data BD0 preceding the image data GD1 by two fields have been conventionally synchronized at an update timing of the image data GD1. Consequently, a color shift has been large, and a backlash has been seen occurring at the time of movie observation.

On the other hand, in the present embodiment, an equation to be used for assignment processing is switched from the equation (1) to the equation (2) at the update timing of the image data GD so that the updated image data GD and image data BD0' preceding the image data GD by one field are synchronized. More specifically, the image pickup system 101 performs second assignment processing using the equation (2) in a first field period serving as a timing at which the image data GD is assigned to the R channel and performs first assignment processing using the equation (1) in a period other than the first field period in the narrow band light observation mode.

As a result, in the image pickup system 101 according to the present embodiment, the image data BD preceding the image data GD1 by two fields is not synchronized in single exposure at the time of the narrow band light observation mode. Thus, the color shift is reduced, and the backlash is resolved at the time of movie observation.

Then, double exposure will be described. The control unit 34 determines whether a luminance value of image data (a fourth image signal) obtained by adding image data BD and image data BD' is less than a predetermined threshold value. If the luminance value of the image data obtained by the addition is less than the predetermined threshold value, a synchronization processing control signal for assigning the image data obtained by adding the image data BD and the image data BD' to the G channel and the B channel is generated and is outputted to the synchronization processing unit 32. Note that if the luminance value of the image data obtained by the addition is the predetermined value or more, the above-described single exposure is controlled.

The synchronization processing unit 32 performs assignment processing using the above-described equation (2) in a first field period serving as a timing at which image data GD has been assigned to the R channel, to assign image data obtained by adding a predetermined proportion of image data BD and image data BD' corresponding to one field to the G channel and the B channel. Note that the predetermined proportion is changed depending on a luminance value of the image data obtained by adding the image data BD and the image data BD'.

On the other hand, the synchronization processing unit 32 performs assignment processing using the above-described equation (1) in a field period other than the first field period serving as the timing at which the image data GD has been assigned to the R channel, to assign image data obtained by adding image data BD corresponding to one field and a predetermined proportion of image data BD' to the G channel and the B channel.

Figure 4A:
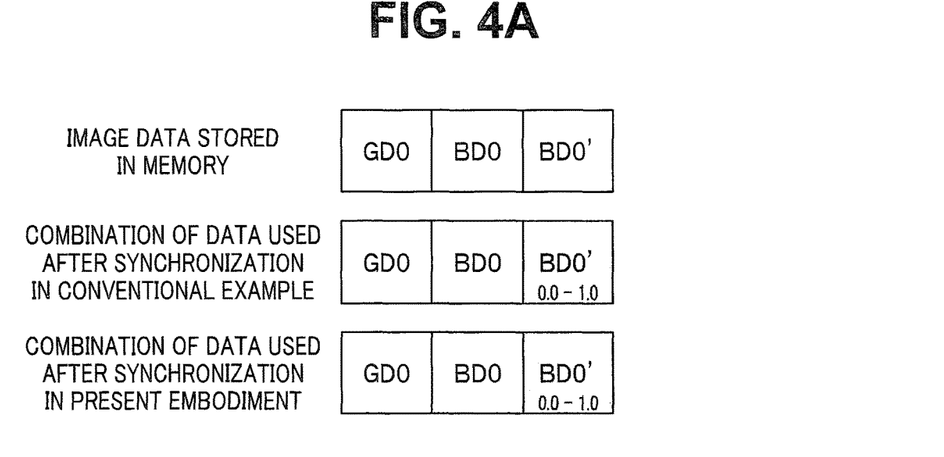
FIG. 4A is a diagram for describing another example of image data synchronized at the time of the narrow band light observation mode.
Figure 4B:
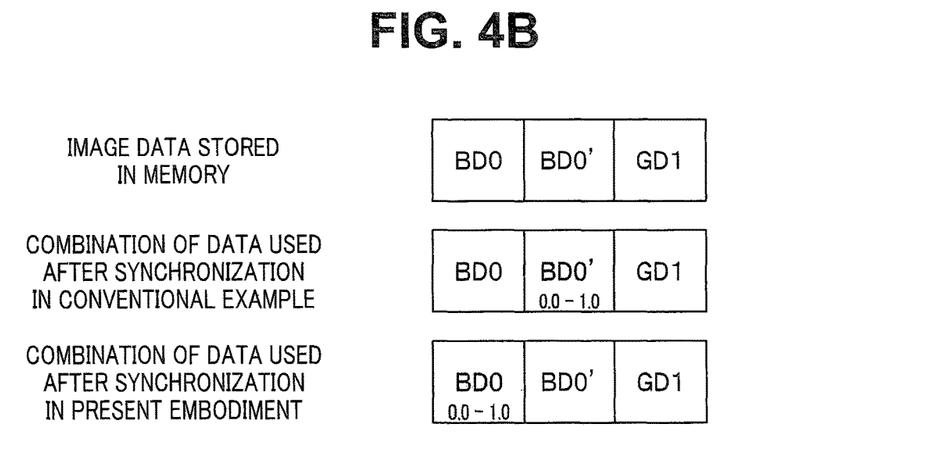
FIG. 4B is a diagram for describing another example of image data synchronized at the time of the narrow band light observation mode.
Figure 4C:
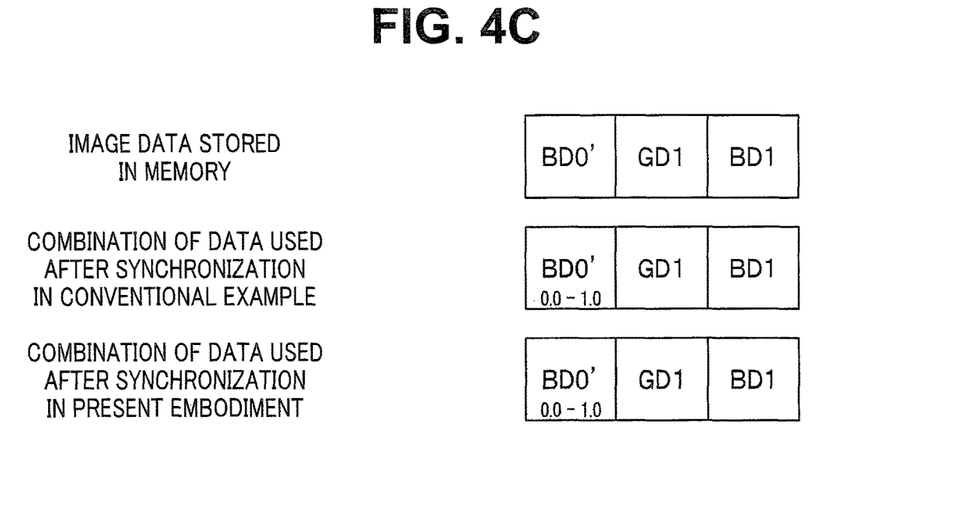
FIG. 4C is a diagram for describing another example of image data synchronized at the time of the narrow band light observation mode.

FIG. 4 is a diagram for describing another example of image data synchronized at the time of the narrow band light observation mode. Note that FIG. 4 illustrates an example of image data to be synchronized when W in the equation (1) and the equation (2) satisfies $0<W \leq 1$ in which case double exposure is performed.

FIG. 4A illustrates a state where image data GD0, BD0, and BD0' sequentially picked up are stored in a memory. In this case, in the conventional example and the present embodiment, assignment processing is performed using the equation (1) so that the image data GD0, the image data BD0, and a predetermined proportion (e.g., more than zero and one or less) of the image data BD0' are synchronized.

FIG. 4B illustrates a state where image data GD1 is further stored in the memory. That is, FIG. 4B illustrates an update timing of the image data GD1. Conventionally, assignment processing has also been performed using the equation (1) at an update timing of the image data GD1. Accordingly, the image data GD1, the image data BD0 preceding the image data GD1 by two fields, and a predetermined proportion of the image data BD0' preceding the image data GD1 by one field have been conventionally synchronized, as illustrated in FIG. 4B.

On the other hand, in the present embodiment, an equation to be used for assignment processing is switched from the equation (1) to the equation (2) at the update timing of image data GD1, and the assignment processing is performed using the equation (2). Accordingly, in the present embodiment, the image data GD1, image data BD0' preceding the image data GD1 by one field, and a predetermined proportion of the image data BD0 preceding the image data GD1 by two fields are synchronized, as illustrated in FIG. 4B.

FIG. 4C illustrates a state where image data BD1 is further stored in the memory. In this case, in the conventional example and the present embodiment, assignment processing is performed using the equation (1), and image data GD1, the image data BD succeeding the image data GD1 by one field, and a predetermined proportion of image data BD0' preceding the image data BD1 by one field are synchronized.

Thus, the updated image data GD1, the image data BD0 preceding the image data GD1 by two fields, and the predetermined proportion of the image data BD0' preceding the image data BD0 by one field have been conventionally synchronized at the update timing of the image data GD1. That is, the image data GD1 and the image data BD0 preceding the image data GD1 by two fields have been mainly synchronized, and the predetermined proportion of the image data BD0' preceding the image data GD1 by one field has been further synchronized. Thus, a color shift has become slightly large.

On the other hand, in the present embodiment, an equation to be used for assignment processing is switched from the equation (1) to the equation (2) at the update timing of the image data GD so that the updated image data GD1 and the image data BD0' preceding the image data GD1 by one field are mainly synchronized, and the predetermined proportion of the image data BD0 preceding the image data GD1 by two fields is further synchronized.

As a result, in the image pickup system 101 according to the present embodiment, the image data BD preceding the image data GD1 by two fields is prevented from being mainly synchronized in double exposure at the time of the narrow band light observation mode. Thus, a color shift is reduced.

Therefore, the image pickup system according to the present embodiment enables a color shift of a video image displayed in frame-sequential narrow band light observation to be reduced.

The present invention is not limited to the above-described embodiment, and various modifications and alterations, for example, can be made without departing from the spirit of the present invention.

What is claimed is:

1. An image pickup system which sequentially irradiates illumination lights of a plurality of colors to pick up an image of an object, the image pickup system comprising:
    a light source unit configured to perform illumination with first illumination light in a wavelength band of a first color and perform illumination with second illumination light in a wavelength band of a second color which is different from the wavelength band of the first color and third illumination light in the wavelength band of the second color emitted temporally after the second illumination light, within a predetermined time period;
    an image pickup unit configured to pick up an image of return light from an object image illuminated with the illumination light emitted from the light source unit for each predetermined period and output an image pickup signal;
    an image generation unit configured to generate, based on the image pickup signal outputted from the image pickup unit, a first image signal responsive to return light of the first illumination light, a second image signal responsive to return light of the second illumination light, and a third image signal responsive to return light of the third illumination light, each corresponding to one field, and sequentially output the image signals; and
    an assignment unit configured to selectively assign the image signals sequentially outputted from the image generation unit to a first color channel, a second color channel, and a third color channel,
    wherein the assignment unit switches first assignment processing for assigning the first image signal to the first color channel and further assigning the second image signal to the second and third color channels and second assignment processing for assigning the first image signal to the first color channel and further assigning the third image signal to the second and third color channels in each of field periods constituting one frame.

2. The image pickup system according to claim 1, wherein the first color channel corresponds to a red color, the second color channel corresponds to a green color, and the third color channel corresponds to a blue color.

3. The image pickup system according to claim 1, wherein the assignment unit assigns the third image signal to the second and third color channels in a first field period serving as a timing at which the first image signal is assigned to the first color channel, as the second assignment processing.

4. The image pickup system according to claim 3, wherein the assignment unit assigns the second image signal to the second and third color channels in a field period other than the first field period set within the predetermined time period, as the first assignment processing.

5. The image pickup system according to claim 1, further comprising
    an image synthesis unit configured to generate a fourth image signal obtained by adding respective luminance values of the second image signal and the third image signal,
    wherein the assignment unit assigns the fourth image signal to the second and third color channels when the luminance value of the image signal generated by the image generation unit is less than a predetermined threshold value.

6. An image processing apparatus comprising:
an image generation unit configured to generate, based on an image pickup signal outputted from an image pickup unit configured to pick up an image of return light from an object image illuminated with illumination light emitted from a light source unit configured to perform illumination with first illumination light in a wavelength band of a first color and perform illumination with second illumination light in a wavelength band of a second color which is different from the wavelength band of the first color and third illumination light in the wavelength band of the second color emitted temporally after the second illumination light, within a predetermined time period for each predetermined period and output the image pickup signal, a first image signal responsive to return light of the first illumination light, a second image signal responsive to return light of the second illumination light, and a third image signal responsive to return light of the third illumination light, each corresponding to one field, and sequentially output the image signals; and
an assignment unit configured to selectively assign the image signals sequentially outputted from the image generation unit to a first color channel, a second color channel, and a third color channel,
wherein the assignment unit switches first assignment processing for assigning the first image signal to the first color channel and further assigning the second image signal to the second and third color channels and second assignment processing for assigning the first image signal to the first color channel and further assigning the third image signal to the second and third color channels in each of field periods constituting one frame.

7. The image processing apparatus according to claim 6, wherein the first color channel corresponds to a red color, the second color channel corresponds to a green color, and the third color channel corresponds to a blue color.

8. The image processing apparatus according to claim 6, wherein the assignment unit assigns the third image signal to the second and third color channels in a first field period serving as a timing at which the first image signal is assigned to the first color channel, as the second assignment processing.

9. The image processing apparatus according to claim 8, wherein the assignment unit assigns the second image signal to the second and third color channels in a field period other than the first field period set within the predetermined time period, as the first assignment processing.

10. The image processing apparatus according to claim 6, further comprising
an image synthesis unit configured to generate a fourth image signal obtained by adding respective luminance values of the second image signal and the third image signal,
wherein the assignment unit assigns the fourth image signal to the second and third color channels when a luminance value of the image signal generated by the image generation unit is less than a predetermined threshold value.

* * * * *